United States Patent [19]

Barthel

[11] 4,364,396

[45] Dec. 21, 1982

[54] CIRCUIT AND METHOD FOR MEASURING PSA OUTPUT AND ENERGY

[75] Inventor: Thomas C. Barthel, Becker, Minn.

[73] Assignee: Medtronic, Inc., Minneapolis, Minn.

[21] Appl. No.: 273,698

[22] Filed: Jun. 15, 1981

[51] Int. Cl.³ .............................................. A61N 1/36
[52] U.S. Cl. ............................................. 128/419 PT
[58] Field of Search ...................... 128/419 PT, 419 D

[56] References Cited

U.S. PATENT DOCUMENTS

| | | | |
|---|---|---|---|
| 3,618,592 | 11/1971 | Stewart | 128/2.05 R |
| 3,756,245 | 9/1973 | Thaler et al. | 128/419 P |
| 3,787,767 | 1/1974 | Hammer et al. | 128/419 D |
| 3,983,476 | 9/1976 | Konopasek | 128/419 D |
| 4,141,367 | 2/1979 | Ferreira | 128/419 PT |
| 4,245,643 | 1/1981 | Benzing et al. | 128/419 PT |
| 4,328,808 | 5/1982 | Charbonnier et al. | 128/419 D |

OTHER PUBLICATIONS

Sum et al., "Digital Cardiac Defibrillator Tester", Med. and Biol. Eng. and Comput., 1979, vol. 17, pp. 710-714.
Jones et al., "Determining Transthoracic Impedance, Delivered Energy . . .", Medical Instrumentation, Nov.-Dec. '81, vol. 15, #6, pp. 380-382.

*Primary Examiner*—V. Millin
*Assistant Examiner*—Mitchell J. Shein
*Attorney, Agent, or Firm*—Glenn W. Bowen; John L. Rooney; Joseph F. Breimayer

[57] ABSTRACT

Apparatus and method for accurately measuring the energy output of a pacing system analyzer or other pulse generator. Voltage measurements are made across the output capacitor before and after the pulse is generated. These voltages are measured by a microprocessor using an analog-to-digital converter and various gating and control circuitry. By using a known value of capacitance for the output capacitor along with the voltages measured before and after the stimulation pulse is generated, the microprocessor can calculate the total amount of energy within the stimulation pulse. This value is displayed on an integral display device. Through the use of additional circuitry, measurements may be made for both atrial and ventricular stimulation pulses in a dual chamber stimulation device. Provisions have also been made for measuring the output energy for constant voltage pulse generators. This technique employs measurement of pulse width.

6 Claims, 14 Drawing Figures

CIRCUIT AND METHOD FOR MEASURING PSA OUTPUT AND ENERGY

BACKGROUND OF THE INVENTION

1. Field of the Invention

The present invention relates generally to medical therapeutic devices, and more specifically relates to electronic devices for stimulating muscle tissue.

2. Description of the Prior Art

It has been the practice for some time to adjust the output energy of a muscle stimulating pulse generator for the purpose of optimizing battery life. Typically, the optimization process has two major steps for cardiac applications. The first step is to position a lead containing the muscle tissue stimulating electrode within the heart. The physical position of the electrode is adjusted to achieve contact to stimulatable tissue using acceptably low energy levels. This adjustment normally takes place using an external pacer device or a pacing system analyzer. Following physical adjustment of the lead, the implantable pulse generator is adjusted to produce an output energy for each stimulation pulse sufficient to reliably stimulate the tissue in contact with the electrode but not so great as to cause premature battery depletion. These two procedures ordinarily occur within the operating room.

To facilitate measurement of the stimulation energy actually produced by a pulse generator (external or internal), several techniques have been employed. The most common technique is to measure the output voltage at a certain point during the stimulation pulse and, by making assumption about the waveshape, to determine the energy therefrom. The assumptions about the waveshape can be made because, of course, the normal stimulation circuitry involves the discharge of an output capacitor through the electrode and into the stimulatable tissue. An improvement in that technique is taught in U.S. Pat. No. 3,983,476 issued to Konopasek. This reference teaches the measurement of the output energy of a defibrillator by measuring the voltage drop across a standard resistor. Konopasek teaches a device that actually integrates over the entire pulse width thereby compensating for any variations in the output waveform and deviations from the assumed waveshape. The major disadvantage of Konopasek is that the discharge is measured only into a standard resistor. This involves the use of a highly precise resistor which may be costly. A further disadvantage is that it measures the stimulation pulse as applied to the standard resistance and not to the stimulatable body tissue. The net result is that the teaching by Konopasek involves a determination of the output energy only into the load resistor.

A method of determining the ohmic resistance of the stimulatable body tissue is taught by Benzing III., et al in U.S. Pat. No. 4,245,643. After such measurement is accomplished, of course, one could then employ the teachings of Konopasek to determine the energy of a discharge not across the standard resistor, but across the actual ohmic resistance found in the stimulatable body tissue. Whereas it is found that this two-step process is sufficient to determine the stimulation energy with sufficient accuracy, it appears to be more complex than desirable.

SUMMARY OF THE INVENTION

The present invention overcomes the disadvantages found in the prior art by directly measuring the energy output of a pulse generator. This measurement is accomplished directly without regard to the type of load into which the discharge occurs. That means that the present invention can measure the energy in an output stimulation pulse which is directed either into a test load or into body tissue.

A further desirable feature of the present invention is that energy is measured directly in a single step process. That means that the attending physician need not perform any calculations within the operating room environment.

A further advantage of the present invention is that it eliminates a number of precision components which would ordinarily be required to perform the energy measurement as done in the prior art. What must be known, however, is the value of the output capacitor of the pulse generator. Fortunately, this is ordinarily a precision component of well-known value.

The present invention measures the voltage across the output capacitor of the pulse generator before and after the stimulation pulse is transmitted. The energy may thus be directly calculated from known formulas as long as the value of the output capacitor is known with sufficient precision.

DETAILED DESCRIPTION OF THE PREFERRED EMBODIMENT

The present invention is described herein as preferably embodied in a pacing system analyzer. This device is used in the operating room for the implant procedure. The preferred pacing system analyzer contains an external pulse generator for both ventricular and atrial chambers. The device also contains the hardware for making the determination of stimulation pulse energy. Other circuitry is contained therein for other monitoring functions. Such a device is the Medtronic ® Model 5311A Pacing System Analyzer. It is important to note, however, that the apparatus and techniques taught herein may also be used equally as effectively in other monitoring devices and in implantable pulse generators.

Figure 1:
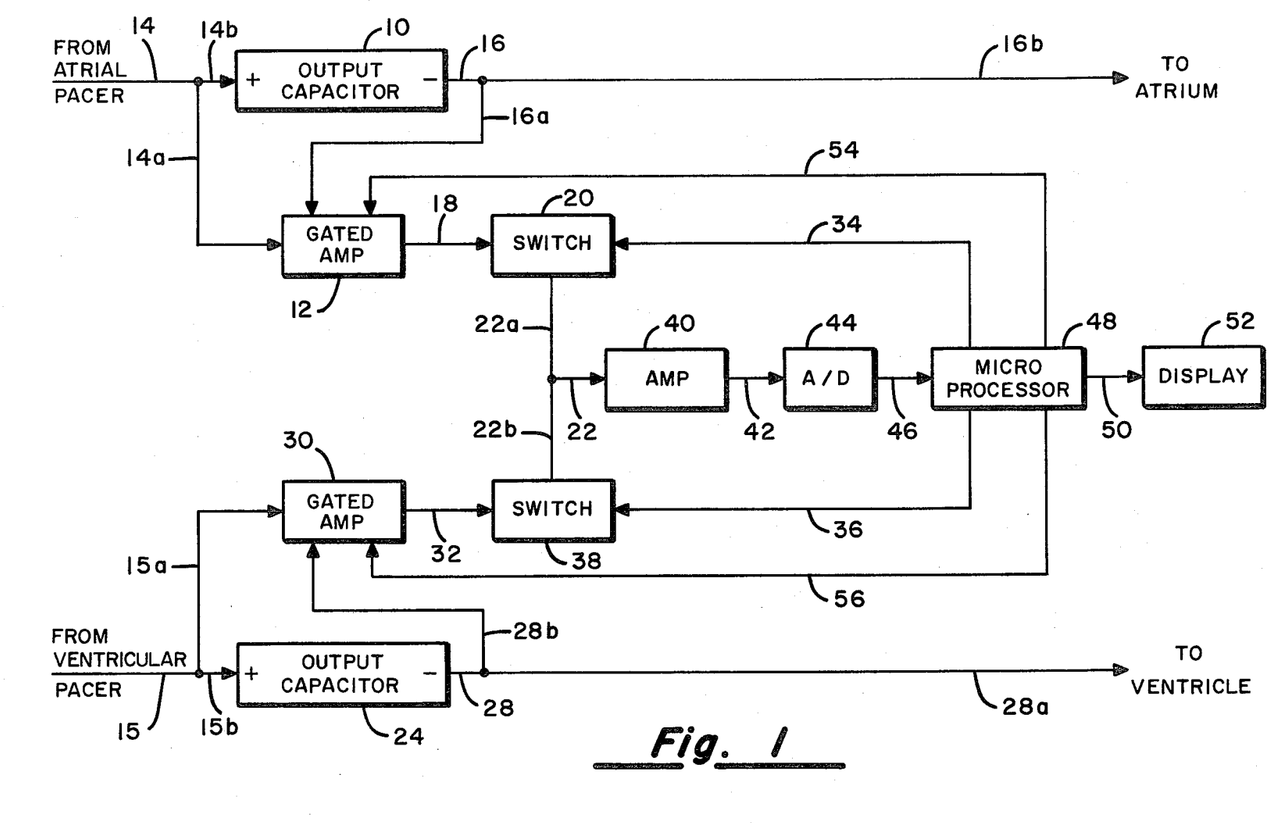
FIG. 1 is an overall block diagram of the apparatus used in the preferred mode of the present invention.

FIG. 1 is a block diagram of the preferred embodiment of the present invention for measuring the energy output of the pacing system analyzer. Notice that the configuration shown in FIG. 1 contains the capability for measuring stimulation pulse energy directed to both the atrium and the ventricle when the atrial and ventricular output capacitors 10 and 24 are discharged. Line 14 is the line which charges the output capacitor 10 via line 14b as shown. This charging current is received from the atrial pacer portion of the pacing system analyzer (not shown). Line 14a is routed to gated amplifier 12. The output of capacitor 10 is directed via line 16 and hence line 16b to the atrium. This corresponds to the lead which is connected electrically via an implanted electrode to the stimulatable tissue within the atrium. Line 16a is also directed to gated amplifier 12.

Gated amp 12 is a differential amplifier having an output which is gated by line 54 from microprocessor 48. At the time when gated amp 12 is enabled via line 54, it supplies an amplified output representative of the differential of lines 14a and 16a (i.e., voltage across output capacitor 10) to switch 20 via line 18. It is important to remember that this voltage is not measured with respect to ground or some other reference point. By measuring directly across output capacitor 10, the inaccuracies associated with the ohmic resistance of body tissue for which compensation is required in the references cited above are removed.

Switch 20 is a linear circuit switch which is controlled by line 34. Line 34 from microprocessor 48 opens or closes the circuit between line 18, the input to switch 20, and line 22a, the output of switch 20. In this manner, microprocessor 48 can via line 34 determine when the output of gated amp 12 will be supplied via line 18 and switch 20 to amp 40 via lines 22a and 22.

Similar circuitry is provided for measuring the energy output of the ventricular stimulation pulse. The output pulse is usually created by the discharge of the previously charged output capacitor. Thus, the signal on line 15 is really the grounding of line 15 through the patient's heart. Output capacitor 24 is charged via lines 15 and 15a as shown. The ventricular stimulation pulse is supplied via lines 28 and 28a. Gated amp 30 functions exactly as does gated amp 12 in that it supplies via line 32 an output proportional to the difference in voltage of lines 15a and 28b whenever enabled to do so by line 56 from microprocessor 48. The output of gated amp 30 is supplied to switch 38 by line 32 as shown. Switch 38 functions in the same manner as switch 20 in that it is a circuit switch which is closed whenever enabled by line 36 from microprocessor 48.

Amp 40 amplifies the output signal on line 22. This is proportional to the voltage measured across output capacitor 10 when microprocessor 48 enables gated amp 12 via line 54 and enables switch 20 via line 34. This is also the voltage across output capacitor 24 when gated amp 30 is enabled by microprocessor 48 via line 56 and switch 38 is enabled via line 36. The output of amp 40 is supplied via line 42 to A/D 44. This device converts the analog signal received via line 42 to a digital signal which is supplied via line 46 to microprocessor 48. Microprocessor 48 controls the system and makes the calculations. It supplies the computed value of energy via line 50 to display 52.

A/D converter 44 is preferably an eight-bit analog-to-digital converter of medium speed. These devices are readily available in monolithic form. An example of such a device is standard model ADC0808 by INTEL, Inc. Similarly, microprocessor 48 may be any convenient eight-bit microprocessor. In the preferred embodiment this is a National Semiconductor Model 8085. Display 52 is preferably an LCD (liquid crystal display) device of common type. Four full digits with decimal point are preferred.

Figure 2:
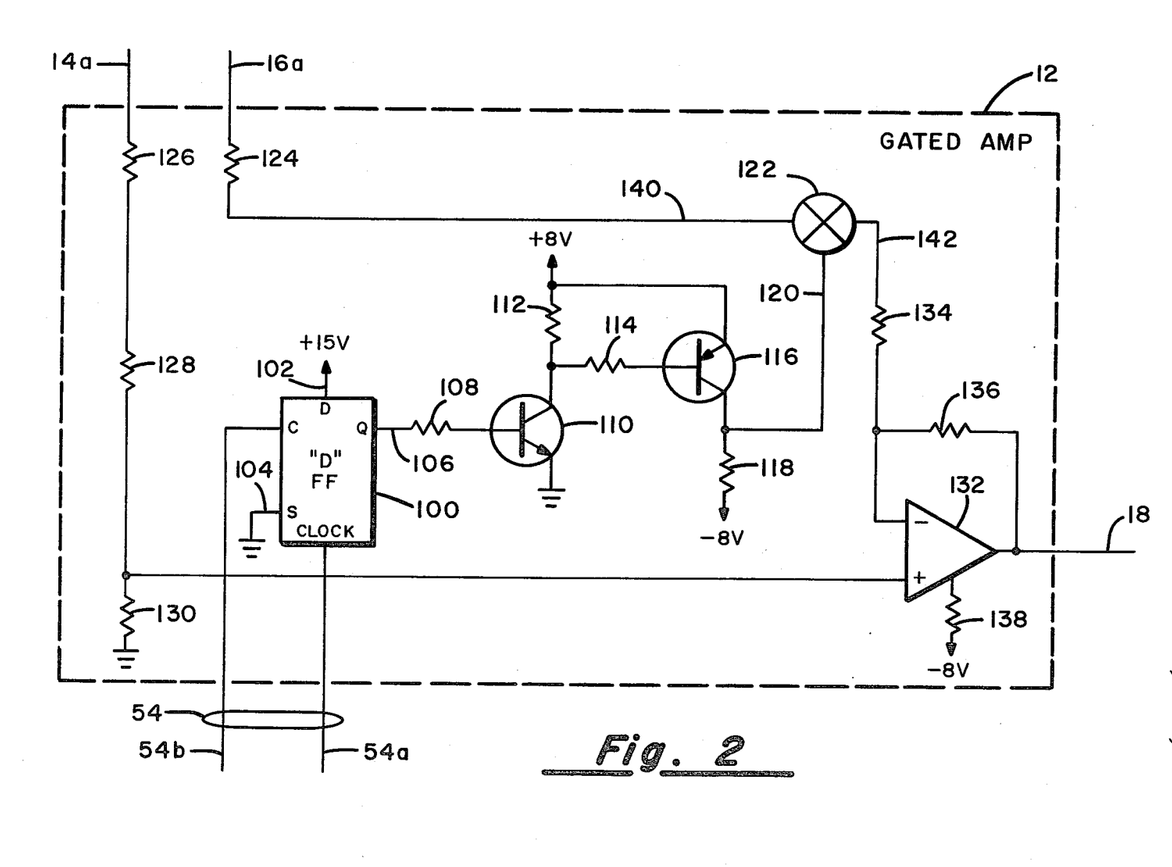
FIG. 2 is an electrical schematic diagram of gated amplifier 12.

FIG. 2 is a detailed electrical schematic of gated amp 12. The circuitry of gated amp 30 is identical to that of gated amp 12 so that a detailed explanation of gated amp 30 is felt unnecessary. The positive side of output capacitor 10 is electrically connected via line 14a to gated amp 12. A voltage divider comprising resistors 126, 128 and 130 are used as input to operational amplifier 132. Resistors 126, 128 and 130 are all 1 megohm high precision, 1 percent resistors. Notice that this presents a high impedance (about 3 megohm) to output capacitor 10. The negative side of output capacitor 10 is connected to gated amp 12 via line 16a. Resistor 124 is also a 1 megohm, 1 percent resistor. The positive input of operational amplifier 132 is received via the voltage divider at the point between resistors 128 and 130. The negative side of operational amplifier 132 is received via 1 megohm, 1 percent resistor 134 and transmission gate 122. Operational amplifier 132 is industry standard part type 8021.

Transmission gate 122 is industry standard part type 4016. Those of ordinary skill in the art will readily recognize that this is a digitally-controlled, linear circuit switch. When enabled by line 120, transmission gate 122 couples the analog signal on line 140 to line 142. Similarly, when disabled by line 120, transmission gate 122 opens the circuit.

Therefore, it can be seen that operational amplifier 132 receives the voltage across output capacitor 10 whenever transmission gate 122 is enabled by line 120.

The state of line 120 is ultimately controlled by the cable 54 received from microprocessor 48 which contains lines 54a and 54b that are connected to the clock input and clear inputs respectively, of "D" flip-flop 100. The data input of "D" flip-flop 100 is connected to the +15 V supply and is therefore always a logical high. The set input of "D" flip-flop 100 is coupled to ground by line 104 so it is always a low. Therefore, line 54b clears "D" flip-flop 100 whenever it contains a logical high. The state of "D" flip-flop 100 changes whenever line 54a transitions to a logical high.

Microprocessor 48 causes line 54b to be a logical high whenever the operator has not selected the measurement of the energy in the atrial stimulation pulse. Conversely, line 54b is a low whenever it is desired to measure the atrial stimulation pulse energy. Whenever measurement is desired, line 54a causes "D" flip-flop 100 to change states whenever it changes from a logical low to a logical high. This permits microprocessor 48 to ultimately control the input to operational amplifier 132.

The output Q of "D" flip-flop 100 is transferred via line 106 and 100 k ohm resistor 108 to NPN transistor 110. Transistor 110 is caused to conduct whenever output Q of "D" flip-flop 100 is high and to be nonconductive whenever output Q of "D" flip-flop 100 is low.

Standard PNP transistor 116 is coupled via 100 k ohm resistor 114 to the collector of NPN transistor 110. 100 k ohm resistor 112 connected to the +8 V power supply provides emitter bias for PNP transistor 116. The 100 k ohm load resistor 118 is connected from the collector of transistor 116 to the −8 V power supply. Whenever transistor 110 conducts transistor 116 conducts. Similarly, whenever transistor 110 does not conduct, transistor 116 is caused not to conduct also.

Whenever transistor 116 is in a conducting state, line 120 goes to a logical high enabling transmission gate 122 to close the circuit between lines 140 and 142. Similarly, whenever transistor 116 is not conducting, line 120 goes to a logical low, disabling transmission gate 122.

Therefore, it can be seen that whenever line 54b clears "D"FF 100, transmission gate 122 is open and the negative input of amplifier 132 is biased solely by 1 megohm resistor 136. Similarly, whenever line 54b is at a logical low "D" flip-flop 100 may be set by the positive transition of line 54a, causing transistor 110 to conduct, causing transistor 116 to conduct, causing transmission gate 122 to be enabled and thereby causing operational amplifier 132 to output, via line 18, a voltage proportional to the voltage across output capacitor 10. As can be seen from FIG. 2, microprocessor 48 can control via lines 54a and 54b the time in which amplifier 132 places a voltage on line 18 which is proportional to the voltage across output capacitor 10. As stated above, this occurs whenever the operator selects the measurement of atrial energy, causing line 54b to be low, and whenever the beginning and ending points to the stimulation pulse are to occur as indicated by the toggling state of line 54a. As also stated above, the ventricular circuitry of gated amp 30 is identical.

Figure 3:
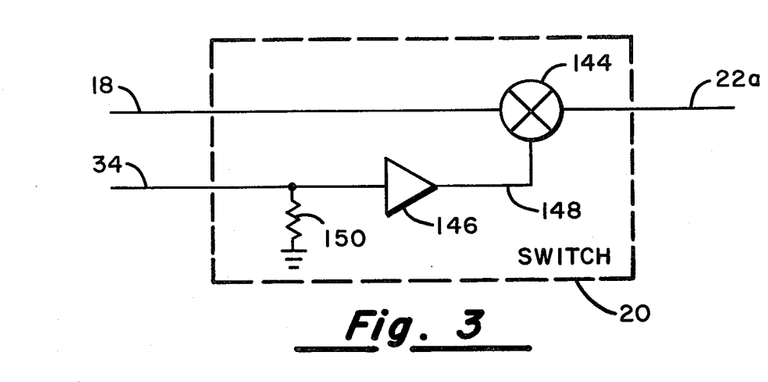
FIG. 3 is an electrical diagram of switch 20.

FIG. 3 is an electrical schematic of switch 20. Referring again to FIG. 1, it can be seen that switch 20 and switch 38 are identical. It is the purpose of switch 20 to switch the output of gated amp 12 received via line 18 into amp 40 via line 22a and line 22. Switch 20 is enabled and disabled by line 34 received from microprocessor 48.

Switch 20 has transmission gate 144 which opens and closes the circuit from line 18 to line 22a. Control of the opening and closing of the circuit is accomplished via line 34, amplifier 146 and line 148. Resistor 150 connected to line 34 has a value of 100 k ohms. Amplifier 146 is required to provide sufficient drive from line 34 to quickly switch transmission gate 144. Switch 20 and switch 38 are required to that amp 140 receives only the atrial or ventricular stimulation pulse signal as determined by microprocessor 48.

Figure 4:
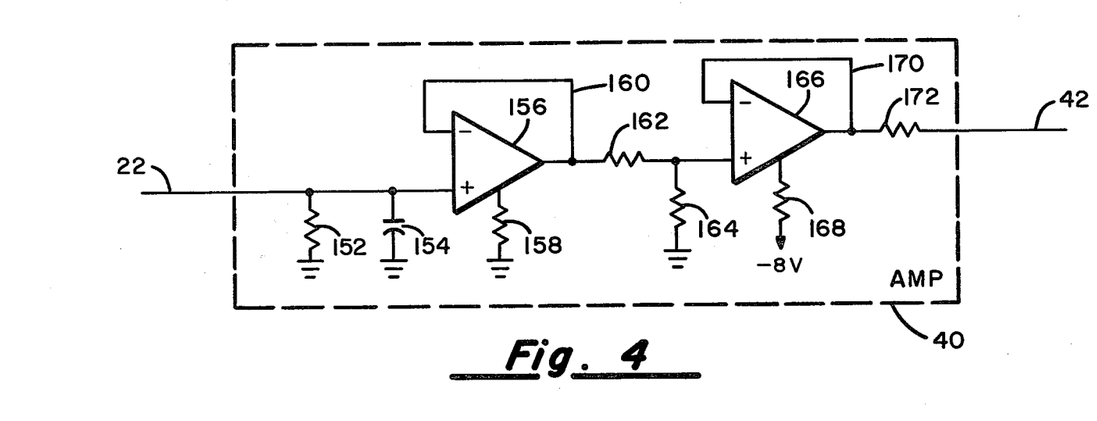
FIG. 4 is an electrical diagram of amplifier 40.
Figure 5A:
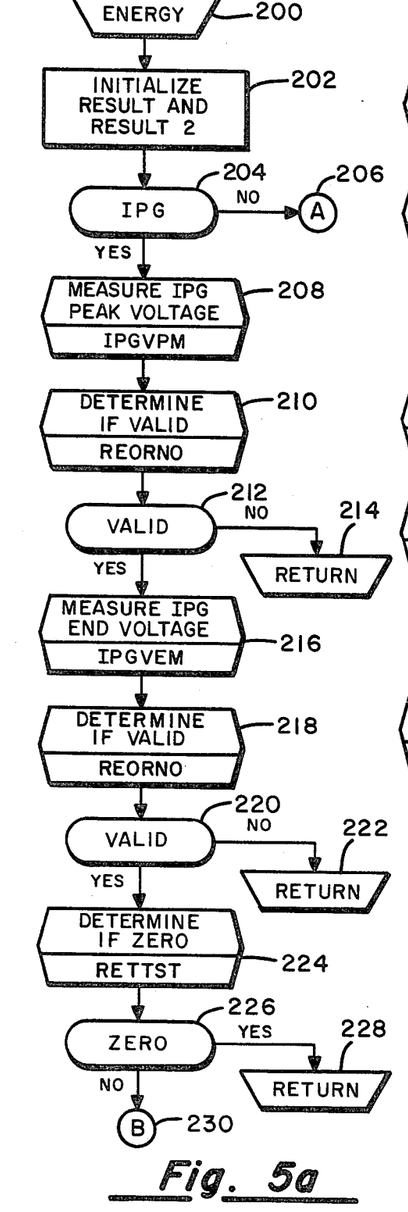
FIG. 5 is a detailed flowchart for the firmware of microprocessor 48 which makes the energy calculations.
Figure 5B:
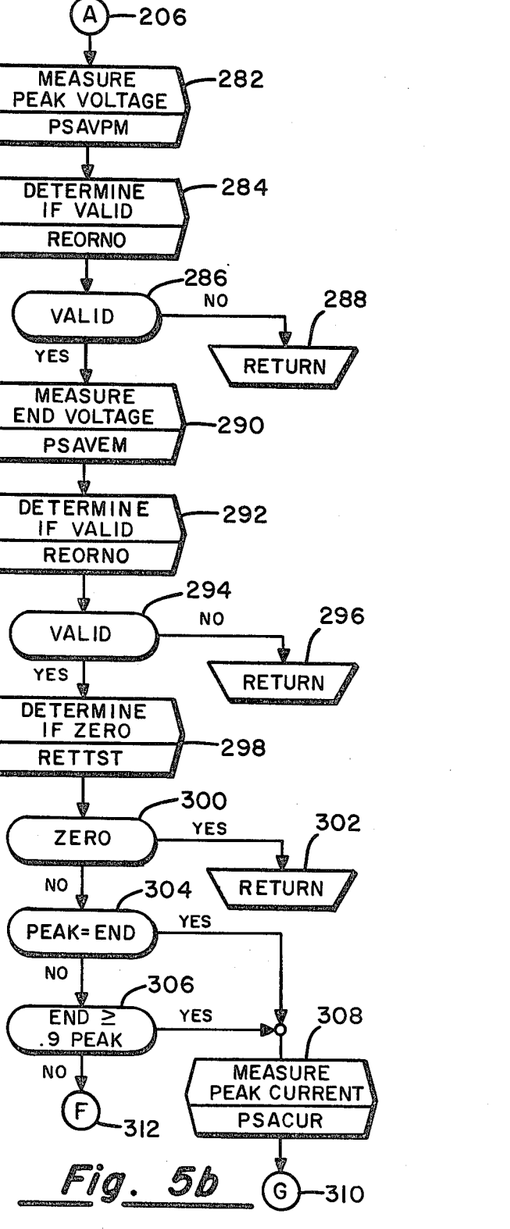
Figures 5C, 5D:
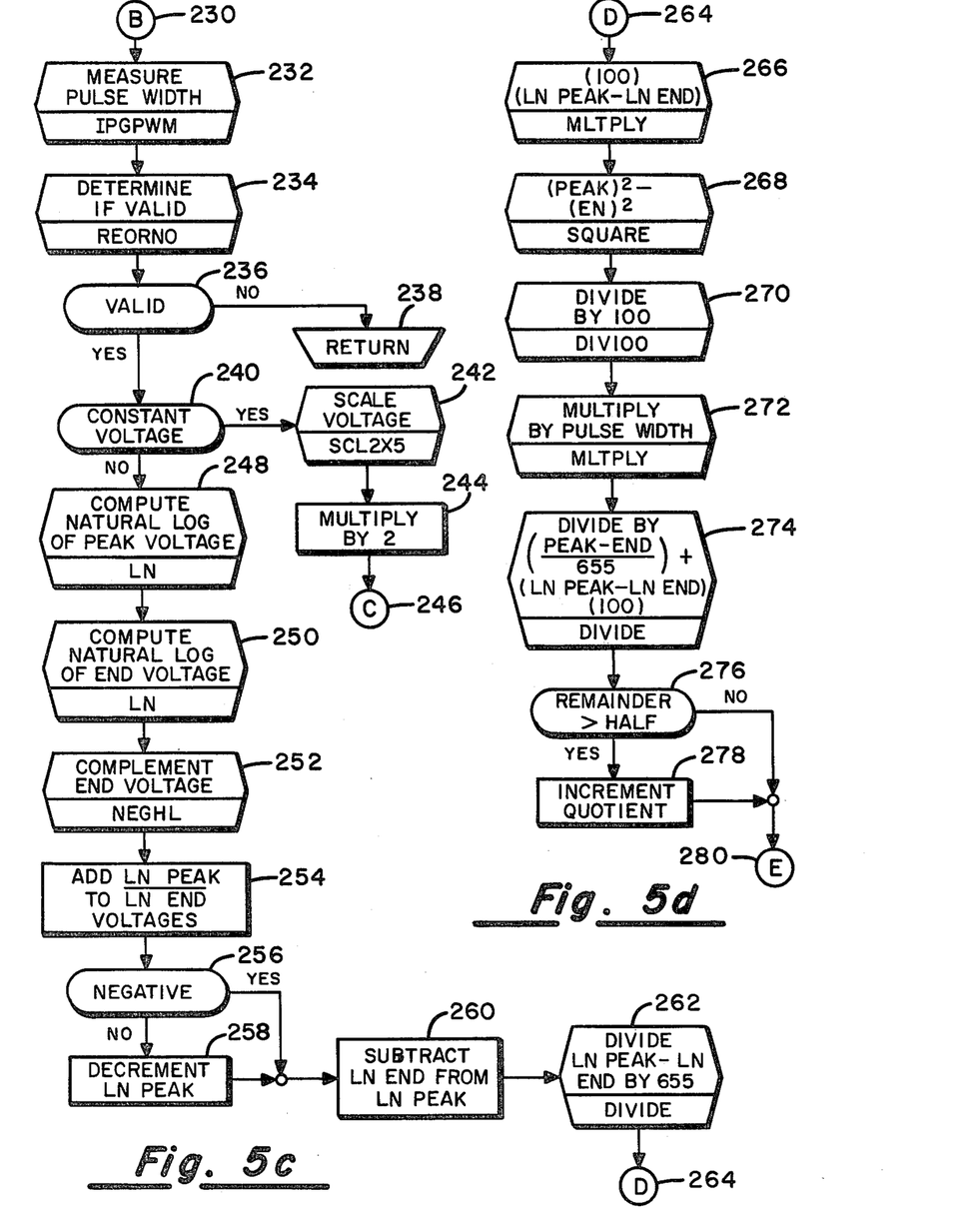
Figure 5E:
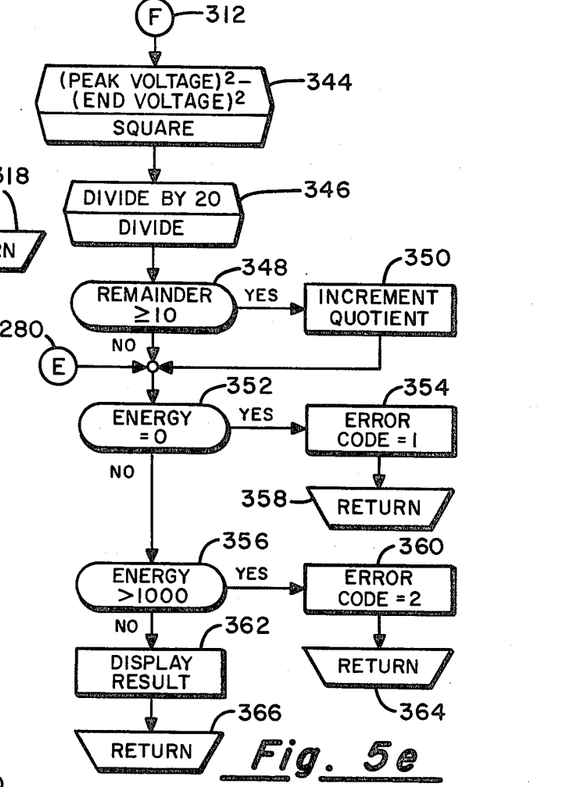
Figure 5F:
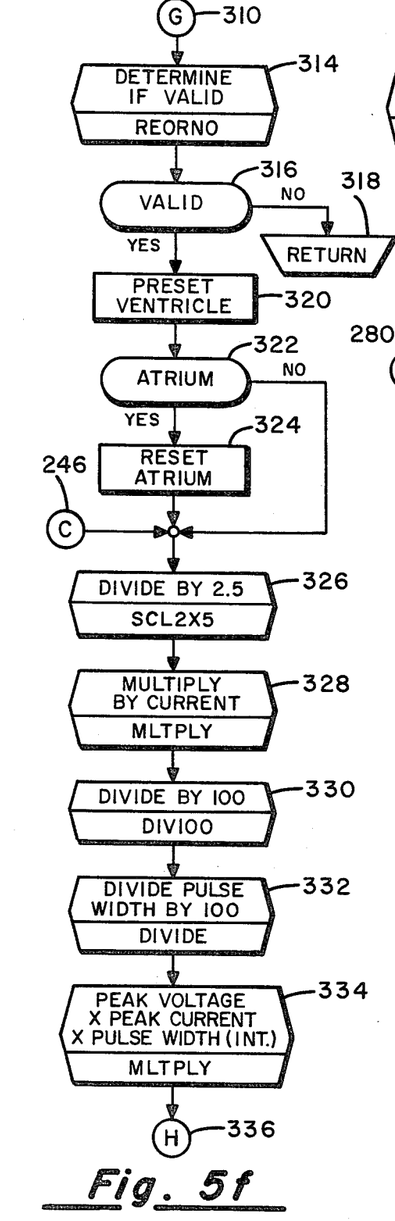
Figure 5G:
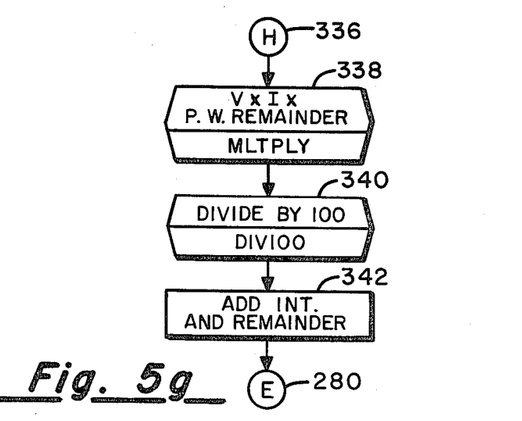

Amp 40 has two stages comprising operational amplifiers 156 and 166 which are industry standard part number 8021 and biasing or coupling components as shown. Resistor 152 has a value of 22 megaohms. Resistor 158 has a value of 10 megaohms. Resistor 162 has a value of 100 k ohms and resistor 164 has a value of 100 k ohms. Resistor 168 has a value of 10 megaohms and resistors 172 has a value of 2.2 k ohms. Capacitor 154 has a value of 0.1 microfarads. FIG. 4 is an electrical schematic of amp 40 which is an ultralinear amplifier used to amplify the signal applied to line 22 and supply it via line 42 to A/D 44.

FIG. 5 is a detailed flowchart for the firmware program which performs the actual energy calculations. This firmware program is a subset of the total firmware which is used in the preferred embodiment of the present invention since the Medtronic ® Model 5311A Pacing System Analyzer performs quite a number of additional functions unrelated to the present invention. The microprocessor chosen for the preferred embodiment is the National Semiconductor Model 8085.

At the selection of operator, subroutine ENERGY is entered at element 200. This corresponds to the desire of the operator to measure the energy found in the stimulation pulse produced by either the external pulse generator (i.e., within the pacing system analyzer) or an implantable pulse generator. Element 202 initializes the values of the variables which store the final result. Element 204 determines whether the measurement is to be computed for an implantable pulse generator or on the pulse generator internal to the monitoring device. If the measurement is to be made on other than an implantable pulse generator, control is transferred via connecting element 206 to element 282. This branch corresponds to the preferred embodiment. As will be seen from the discussions below, this measurement is quite similar to that performed for the implantable pulse generator. However, the value of the output capacitor must be determined for the implantable pulse generator whereas this value is known for the external pulse generator.

For the case wherein the energy to be measured is from a stimulation pulse generated from within the pacing system analyzer, the value of C is known. In this case, energy may be defined as 0.5×the value of the peak voltage squared−the value of the ending voltage squared×the value of the capacitor which is known. In the preferred embodiment, the output capacitor 10 and output capacitor 24 each have a value of approximately 10 microfarads. This value will be seen in the calculations below.

The atrial and ventricular stimulation pulse energy measurements are performed in the same manner. To refer to the hardware description therefor, one can view atrial measurement, but should keep in mind that ventricular measurements are accomplished in the same fashion. Element 282 calls procedure PSAVPM which actually measures the peak voltage of the pulse generator within the pacing system analyzer. Referring back to FIG. 1, this corresponds to holding line 54b to a logical low and holding lines 54a and 34 to logical highs. This can be accomplished easily by microprocessor 48 using an I/O device such as National Semiconductor Model NSC810.

Element 284 calls procedure REORNO to determine if the value is valid. This determination is simply whether or not the value measured is all 1's which is not defined. Element 286 determines whether or not procedure REORNO found validity. If the value found was not valid, return is made via element 288. Assuming the measured value peak voltage was not all 1's, element 290 calls procedure PSAVEM to measure the end voltage of the pulse generator output capacitor 10. Again referring to FIG. 1 it can be seen that, in this fashion, the firmware program within microprocessor 40 has caused the voltage across output capacitor 10 to be measured directly before and immediately after the stimulation pulse.

Referring again to FIG. 3, element 292 calls procedure REORNO again to determine whether the ending voltage is valid. Element 294 determines if validity was found and if not, return is made via element 296. Assuming that the ending voltage measured was not all 1's, element 298 transfers control to procedure RETTST to determine if either voltage measured was 0. The operation of this subroutine is explained in more detail below.

Element 300 determines whether or not one of the voltages was 0 and if yes, return is made through element 302. If neither of the two voltages measured were 0, element 304 determines whether the peak and ending voltages were the same. This will be the case when a constant voltage stimulation pulse is produced. Notice that element 306 determines whether the ending voltage is within 90 percent of the peak voltage. Again, in the abnormal case where this is true, control is transferred to PSACUR via element 308 to measure the peak current.

Element 312 is the continuation of the energy measurement for the pacing system analyzer in the preferred constant current situation. Element 344 calls specialized procedure SQUARE which takes the difference between the squared peak voltage and squared end voltage. Element 346 calls procedure DIVIDE which is a division by 20. Notice this accomplishes multiplication by the value of C, the value of output capacitor 10, multiplication by the constant ½ and scaling—all simultaneously. The remainder is viewed at element 348.

Element 350 causes the quotient to be rounded off if the remainder is greater than 10.

The other types of energy calculations (explained below) are merged via element 280. Element 352 determines whether or not the measured value for energy is equal to 0. If the answer is yes, element 354 fetches an error code of 1 and return is made via element 358. If element 352 finds that the energy is not equal to 0, element 356 determines whether or not the energy is greater than 1,000. This would correspond to an unrealistically high value for energy. If this determination is made, element 360 fetches an error code of 2 and return is made via element 364. Assuming that the energy value is within range, the result is displayed at element 362 via display 52 and return is made via element 366.

The operations performed between elements 314 and 342 are used to compute energy for the constant voltage pulse generators. Having just measured the peak current at element 308, element 314 transfers control to subroutine REORNO to determine whether the current read was all 1's. Element 316 returns control via element 318 to the calling program if the current value read was improper. Assuming that the current value read was valid, element 320 presets the determination to the ventricle. This indication is for display purposes only. Element 322 next determines whether or not this is from the atrium. If it is not, control is sent to element 326. If the atrium has been selected, however, element 324 resets the flag to display the atrium. Point 246 represents the entry point for the IPG constant voltage measurement. This entry is discussed below.

At element 326, control is sent via subroutine SCL2X5 to scale the current value. Element 328 next calls subroutine MLTPLY to multiply the current. Procedure DIV100 is called by element 330 to scale the resultant by a factor of 100. Element 322 divides the pulse width by 100 by calling procedure DIVIDE.

At this point, the peak voltage, peak current and pulse width have all been measured, validated and scaled. Element 334 calls procedure MLTPLY to multiply these three quantities. The remainder is multiplied at element 338. The resultant is scaled by procedure DIV100 at element 340. The resultant and the remainder are added together at element 342. From element 280 the control will be sent to that part of the procedure wherein the energy value computed is validated and displayed.

Element 208 is arrived at after element 204 determines that implantable pulse generator pulse energy is to be measured. Procedure IPGVPM is called by element 208 to measure the peak voltage across the output capacitor. Element 210 calls procedure REORNO to determine if the resulting voltage is all 1's. If the measured voltage is invalid, element 212 transfers control to element 214 which returns control to the calling routine. Assuming that element 212 finds the measured value to be valid, element 216 transfers control to procedure IPGVEM to measure the ending voltage. Element 218 calls procedure REORNO to determine if the ending voltage measured is all 1's. If this value is invalid, element 220 sends control to element 222 for a return. Assuming that the value measured is valid, element 224 sends control to procedure RETTST to determine if either the peak or ending voltage values is 0. If either is 0, element 300 sends control to the calling procedure via a return element 302. Assuming that neither of the values measured was 0, element 232 transfers control to procedure IPGPWM to measure that pulse width. A number of ways are available for the measurement of pulse width. Pulse width measurement is required to determine the value of the implantable pulse generator output capacitor. Procedure REORNO is called by element 234 to determine if the pulse width is valid. Element 236 causes the return at element 238 if not valid.

Element 240 determines whether the output from the implantable pulse generator is a constant voltage output. A number of manufacturers produce implantable pulse generators which are configured in this fashion. The constant voltage output must be measured in a different fashion and involves the use of the pulse width measurement made at element 232. Although this particular measurement technique is not the preferred method, it is discussed herein for the purposes of completeness. Element 242 calls procedure SCL2×5 to scale the voltage. Notice that the peak and end voltages are the same. Element 244 multiplies the scaled voltage by two and transfers control via element 246 to complete the computations as discussed above.

Assuming that the implantable pulse generator has not produced a constant voltage as measured by element 240, control is transferred to procedure LN via element 248 to compute the natural log of the peak voltage. Similarly, element 250 transfers control to procedure LN to compute the natural log of the ending voltage. Element 254 then calls procedure NEGHL which complements the ending voltage. Element 254 adds the natural log of the peak voltage to the complement of the natural log of end voltage. Element 256 determines whether the result is negative. If the result is not negative, element 258 decrements the natural log of the peak voltage.

Element 260 subtracts the natural log of the ending voltage from the natural log of the peak voltage. Element 262 transfers control to procedure DIVIDE which divides the difference between the natural log of the peak voltage and the natural log of the end voltage by the constant 655. Division by this constant enables the firmware to properly scale the value of the peak voltage minus the end voltage by a factor of 16.

Element 266 transfers control to procedure MLTPLY which multiplies the difference in the natural log of the peak and ending voltages by 100. Control is then transferred to procedure SQUARE by element 268 to obtain the difference of the squares of the peak and ending voltages. Procedure SQUARE is explained in greater detail below.

Element 270 calls procedure DIV100 to divide the resultant by 100. Again, this procedure is discussed in more detail below. Element 272 calls procedure MLTPLY to multiply the resultant by the pulse width. Element 274 then calls procedure DIVIDE and the round-off for the remainder is handled at element 276. If the remainder is greater than one-half, then element 278 increments the quotient. Control is then transferred via connector 280 to element 352.

It can be seen that the logic between element 204 and element 280 is used to compute the value of the capacitance of an implantable pulse generator wherein the capacitor value is not known. This computation takes the form of energy=pulse width×(peak voltage squared−ending voltage squared)/the natural log of (peak voltage/end voltage). This is required in the implantable pulse generator case wherein the value of the output capacitor is not known.

Thus, it can be seen that the preferred embodiment computes energy in three basic ways. The preferred approach operates with a known value of capacitance for the output capacitor. This is the case wherein the energy of the output pulse of the pacing system analyzer is measured. For this case, only the peak and ending voltages need be measured. The energy is then computed as one half of the capacitance × the quantity peak voltage squared — end voltage squared.

The second technique is for implantable pulse generators wherein the value of the capacitor is not known. In this case, the peak voltage, end voltage and pulse width determinations are made to determine the value of the output capacitor. The third approach is used for either the implantable pulse generator or the pacing system analyzer. It calculates energy using pulse width and peak current for constant voltage output stimulation pulses.

Figures 6, 7, 8:
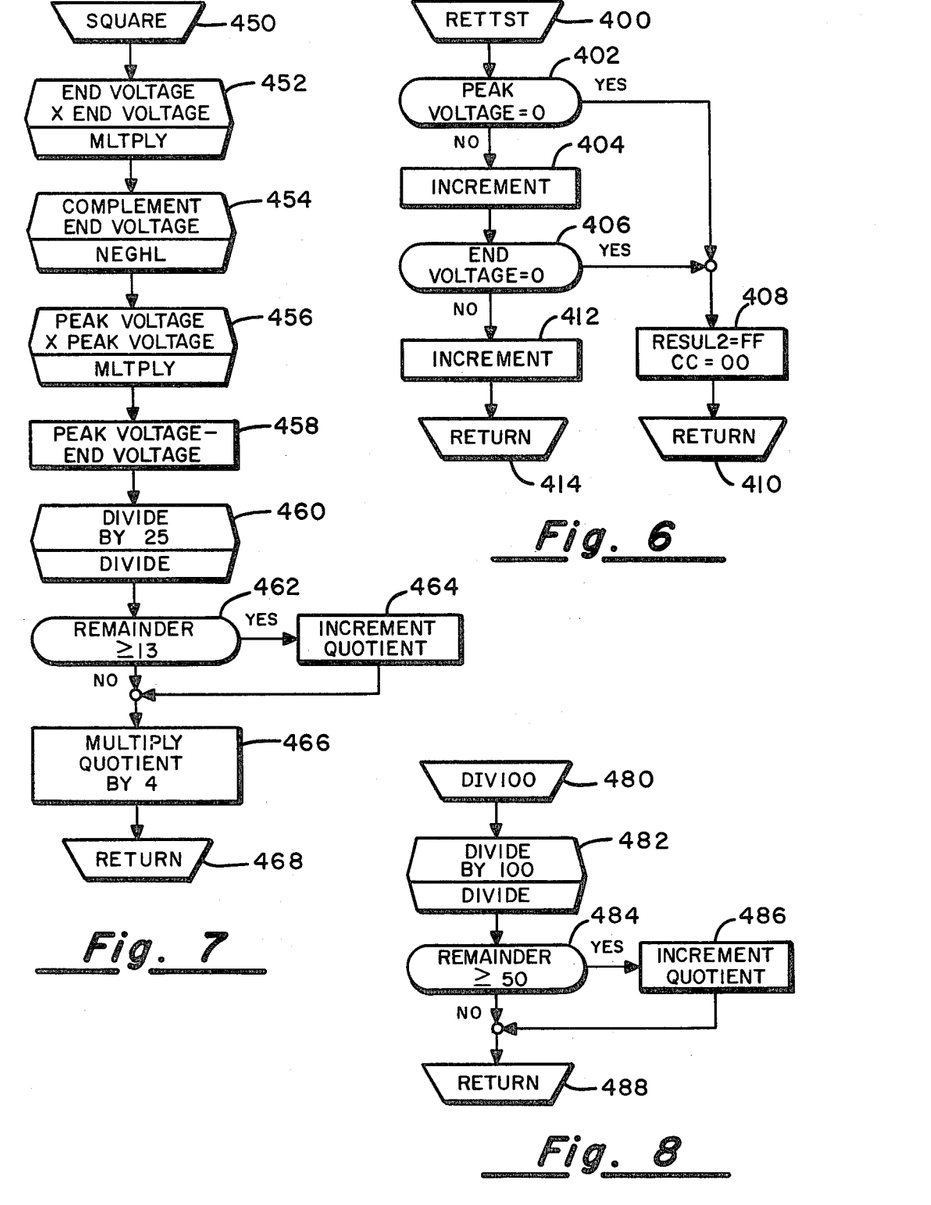
FIG. 6 is a flowchart for subroutine RETTST.
FIG. 7 is a flowchart for subroutine SQUARE.
FIG. 8 is a flowchart for subroutine DIV100.

FIG. 6 is flowchart for subroutine RETTST. Its function is to prepare the display output in the case wherein no stimulation pulse is generated. This, of course, will occur when a natural R-wave is sensed in the demand pacing mode. For example, this occurs when the normal physiological pacing is produced by the body. Element 402 determines whether the peak voltage is equal to 0. If that is not the case, element 404 increments the counter and element 406 determines whether the end voltage is equal to 0. If the end voltage is not equal to 0, element 412 increments the counter again and return is made via element 414. Notice that, if either of the peak voltage or the end voltage is determined to be 0 by elements 402 or 406 respectively, control is returned via element 410 after element 408 sets the display output values RESUL2 and CC2 known values.

FIG. 7 is a flowchart for subroutine SQUARE. This subroutine is used to subtract the square of the ending voltage from the square of the peak voltage. Element 452 calls procedure MLTPLY which multiplies the ending voltage × ending voltage. This results in the ending voltage squared. Element 454 calls procedure NEGHL which complements the squared ending voltage. Element 456 calls MLTPLY to square the peak voltage. The difference is found at element 458 by adding the squared peak voltage to the complemented squared end voltage. Element 460 calls procedure DIVIDE to scale the result by a factor of 25. Element 462 determines whether the remainder is greater than one-half. If the answer is yes, element 464 increments the quotient. This, of course, takes care of the round-off problem. Element 466 then multiplies the quotient by 4 to scale it for further processing. Return is via element 468.

FIG. 8 is a flowchart for subroutine DIV100. This procedure merely scales a quantity by the factor of 100. Element 482 calls procedure DIVIDE which divides by 100. Element 484 determines whether the remainder is greater than one-half. Element 486 increments the quotient by properly round-off as required. Element 488 returns to the calling program.

It can be thus seen from the foregoing discussion that the disclosed apparatus readily computes the energy of a cardiac pacer stimulation pulse as directed either into a fixed load or into body tissue at the preference of the operator. Those of ordinary skill in the art will be able to readily apply these teachings to other energy measurement tasks within the medical electronics field.

What is claimed is:

1. An apparatus for indicating an energy content of a body stimulating electrical pulse produced by a discharge of a capacitor having a given capacitance comprising:
   means responsively coupled to said capacitor for measuring a first voltage drop across said capacitor prior to said discharge and a second voltage drop subsequent to said discharge;
   means responsively coupled to said measuring means for computing said energy content from said first voltage drop, said second voltage drop, and said given capacitance; and
   means responsively coupled to said computing means for displaying said energy content.

2. An apparatus according to claim 1 further comprising means responsively coupled to said computing means for determining said given capacitance.

3. An apparatus according to claim 1 or claim 2 wherein said measuring means further comprises an analog-to-digital converter.

4. An apparatus according to claim 3 wherein said computing means further comprises a microcomputer.

5. A method for determining an output energy of a body stimulating pulse produced by a discharge of a capacitor having a given capacitance comprising:
   (a) sensing a first voltage drop across said capacitor prior to said discharge;
   (b) converting said first voltage drop to a first digital quantity;
   (c) sensing a second voltage drop across said capacitor subsequent to said discharge;
   (d) converting said second voltage drop to a second digital quantity;
   (e) squaring said first digital quantity;
   (f) squaring said second digital quantity;
   (g) subtracting the square of said second digital quantity from the square of said first digital quantity producing a partial resultant; and
   (h) multiplying said partial resultant by one-half of said given capacitance.

6. A method according to claim 5 further comprising determining said given capacitance before step (h).

* * * * *

UNITED STATES PATENT AND TRADEMARK OFFICE
CERTIFICATE OF CORRECTION

PATENT NO. : 4,364,396
DATED : December 21, 1982
INVENTOR(S) : Thomas C. Barthel It is certified that error appears in the above-identified patent and that said Letters Patent are hereby corrected as shown below:

Column 5,
　　　Line 10, "to" should be --of--;

Line 28, "to" should be --so--;

Line 34, "megaohms" should be --megohms--;

Line 35, "megaohms" should be --megohms--;

Line 37, "megaohms" should be --megohms--;

Column 7,
　　　Line 36, "322" should be --332--;

Column 10,
　　　Line 3, "by" should be --to--.

Signed and Sealed this

Twenty-sixth Day of April 1983

[SEAL]

Attest:

Attesting Officer

GERALD J. MOSSINGHOFF
Commissioner of Patents and Trademarks